United States Patent
Seeber

(10) Patent No.: US 10,092,365 B2
(45) Date of Patent: Oct. 9, 2018

(54) APPARATUS AND METHOD FOR ROBOT-ASSISTED SURGERY

(71) Applicant: avateramedical GmbH, Jena (DE)

(72) Inventor: Marcel Seeber, Jena (DE)

(73) Assignee: avateramedical GmbH (DE)

(*) Notice: Subject to any disclaimer, the term of this patent is extended or adjusted under 35 U.S.C. 154(b) by 160 days.

(21) Appl. No.: 15/172,741

(22) Filed: Jun. 3, 2016

(65) Prior Publication Data
US 2016/0361122 A1 Dec. 15, 2016

(30) Foreign Application Priority Data

Jun. 12, 2015 (DE) .................. 10 2015 109 371

(51) Int. Cl.
*A61B 34/20* (2016.01)
*A61B 34/00* (2016.01)
(Continued)

(52) U.S. Cl.
CPC .............. *A61B 34/20* (2016.02); *A61B 34/30* (2016.02); *A61B 34/32* (2016.02); *A61B 34/70* (2016.02);
(Continued)

(58) Field of Classification Search
None
See application file for complete search history.

(56) References Cited

U.S. PATENT DOCUMENTS 6,757,557 B1* 6/2004 Bladen .................. A61B 5/6806
128/899
7,666,191 B2 2/2010 Orban, III et al.
(Continued)

FOREIGN PATENT DOCUMENTS

DE 69112538 T2 3/1996
DE 69322202 T2 7/1999
(Continued)

OTHER PUBLICATIONS

European Search Report dated Oct. 5, 2016 and received on Oct. 12, 2016 (in German without translation) (10 pages).

*Primary Examiner* — Truc M Do
(74) *Attorney, Agent, or Firm* — Harness, Dickey & Pierce, P.L.C.

(57) ABSTRACT

An apparatus for robot-assisted surgery as well as a method for assisting the positioning of a manipulator arm of an apparatus for robot-assisted surgery. An instrument unit is connected to a coupling unit of the manipulator arm. The instrument unit has a surgical instrument with an instrument shaft, the proximal end of which is passable through a body orifice of a patient to a target area. When connecting the instrument unit to the coupling unit the distance vector (V), which is orthogonal to the longitudinal axis of the instrument shaft of the surgical instrument, between the longitudinal axis and the target area defined by the coordinates ($x_z$, $y_z$, $z_z$) is determined. A first control information is generated when the amount of the determined distance vector (V) has and/or falls below a first preset value. An output unit outputs a signal dependent on the first control information.

16 Claims, 14 Drawing Sheets

(51) Int. Cl.
  *A61B 34/30* (2016.01)
  *A61B 34/32* (2016.01)
  *A61B 17/00* (2006.01)
  *A61B 90/00* (2016.01)

(52) U.S. Cl.
  CPC ............ *A61B 2017/00115* (2013.01); *A61B 2017/00128* (2013.01); *A61B 2034/2059* (2016.02); *A61B 2034/305* (2016.02); *A61B 2090/061* (2016.02)

(56) References Cited

U.S. PATENT DOCUMENTS

| | | | | |
|---|---|---|---|---|
| 7,809,421 | B1* | 10/2010 | Govari | G01V 13/00 324/200 |
| 8,554,368 | B2* | 10/2013 | Fielding | A61B 19/2203 700/245 |
| 9,687,307 | B2* | 6/2017 | Wu | A61B 34/20 |
| 9,855,662 | B2* | 1/2018 | Ruiz Morales | B25J 13/085 |
| 2002/0123825 | A1* | 9/2002 | Ohtsuki | B25J 9/1689 700/245 |
| 2004/0143178 | A1* | 7/2004 | Leitner | A61B 34/20 600/407 |
| 2005/0020911 | A1* | 1/2005 | Viswanathan | A61B 6/12 600/424 |
| 2005/0085718 | A1* | 4/2005 | Shahidi | A61B 1/04 600/424 |
| 2006/0241405 | A1* | 10/2006 | Leitner | A61B 5/103 600/426 |
| 2006/0258938 | A1* | 11/2006 | Hoffman | A61B 1/00193 600/424 |
| 2006/0276686 | A1* | 12/2006 | Tsuji | A61B 5/06 600/117 |
| 2007/0142970 | A1* | 6/2007 | Burbank | B25J 19/0029 700/251 |
| 2009/0143907 | A1* | 6/2009 | Demathelin | B25J 17/0266 700/245 |
| 2009/0171374 | A1* | 7/2009 | Omori | A61B 34/71 606/130 |
| 2010/0069920 | A1* | 3/2010 | Naylor | A61N 5/1049 606/130 |
| 2010/0076305 | A1 | 3/2010 | Maier-Hein et al. | |
| 2010/0094312 | A1* | 4/2010 | Ruiz Morales | B25J 13/085 606/130 |
| 2011/0152871 | A1 | 6/2011 | Park et al. | |
| 2012/0035507 | A1* | 2/2012 | George | A61B 1/00147 600/587 |
| 2012/0226145 | A1* | 9/2012 | Chang | A61B 34/30 600/424 |
| 2012/0289764 | A1* | 11/2012 | Murakami | A61N 2/002 600/11 |
| 2013/0325029 | A1* | 12/2013 | Hourtash | B25J 9/1607 606/130 |
| 2013/0345718 | A1* | 12/2013 | Crawford | A61B 17/025 606/130 |
| 2014/0088410 | A1* | 3/2014 | Wu | A61B 5/064 600/424 |
| 2014/0148820 | A1* | 5/2014 | Ogawa | A61B 17/29 606/130 |
| 2014/0171957 | A1 | 6/2014 | McNeela et al. | |
| 2014/0343404 | A1* | 11/2014 | Razzaque | A61B 8/0841 600/424 |
| 2016/0157751 | A1* | 6/2016 | Mahfouz | A61B 5/062 600/409 |
| 2017/0312047 | A1* | 11/2017 | Swarup | A61B 90/50 |
| 2017/0333145 | A1* | 11/2017 | Griffiths | A61B 34/35 |

FOREIGN PATENT DOCUMENTS

| | | |
|---|---|---|
| DE | 10242953 A1 | 3/2004 |
| WO | WO-2006-091494 A1 | 8/2006 |

\* cited by examiner

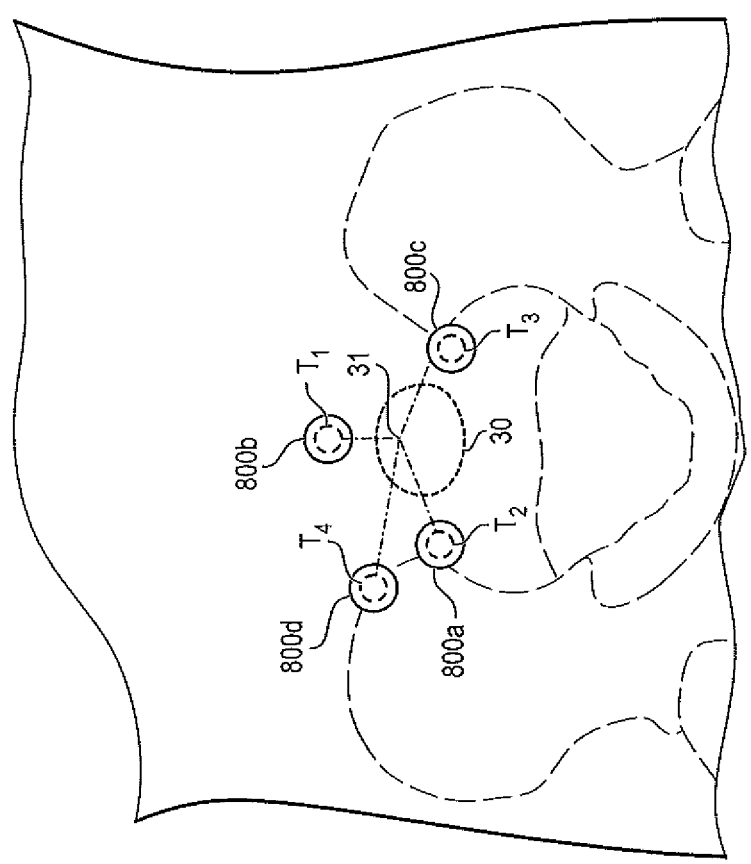

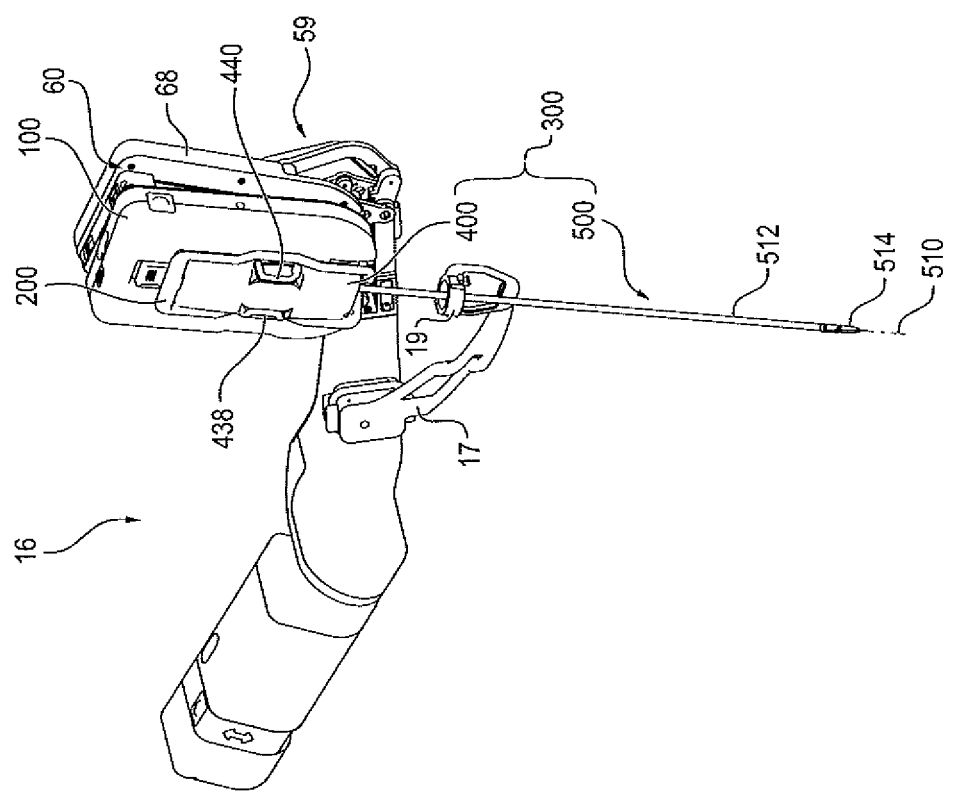

APPARATUS AND METHOD FOR ROBOT-ASSISTED SURGERY

CROSS-REFERENCE TO RELATED APPLICATION

This application claims the benefit and priority of DE 10 2015 109 371.5, filed Jun. 12, 2015. The entire disclosure of the above application is incorporated hereby by reference.

BACKGROUND OF THE INVENTION

Technical Field

The invention relates to an apparatus and a method for robot-assisted surgery for assisting in positioning a manipulator arm in a coordinate system of an apparatus for robot-assisted surgery. The apparatus has an instrument unit which comprises a surgical instrument with an instrument shaft. The proximal end of the instrument shaft is passable through a body orifice of a patient to a target area. The instrument unit is connectable to a manipulator arm of the apparatus.

Discussion

In minimally-invasive surgery, so-called telemanipulator systems, also referred to as robot-assistance systems or generally as apparatus for robot-assisted surgery, are increasingly used. By means of an apparatus for robot-assisted surgery, surgical instruments are controlled in their position and orientation on the basis of user inputs. The surgical instruments are further mechanically, electrically and/or optically coupled to the telemanipulator system so as to be able to implement an active positioning and orientation of the surgical instrument as well as a desired actuation of a surgical instrument. For this, the surgical instruments, which in addition to instruments with end effectors also comprise endoscopes and medical apparatuses to be operated, have a coupling interface which may be designed as a coupling unit and is also referred to as sterile unit. The apparatus for robot-assisted surgery further has at least one manipulator arm, at the proximal end of which the coupling unit is provided, to which the sterile unit is connectable in order to enable the mechanical, electrical and/or optical coupling between the manipulator arm and the surgical instrument.

Apparatuses in which the manipulator arms and the coupling units of the manipulator arms are not sterile and the surgical instruments are sterile are known. The sterile surgical field is protected against the non-sterile elements of the telemanipulator system by means of a sterile cover. This sterile cover may comprise a sterile lock which is provided between the coupling unit of the manipulator arm and the sterile unit of a surgical instrument. Such a sterile lock enables the sterile covering of the non-sterile coupling elements of the coupling unit of the manipulator arm after separating the sterile unit of the instrument unit from the manipulator arm. Such an arrangement with a sterile lock is, for example, known from the non-prepublished patent application DE 10 2014 117 407.0 and DE 10 2014 117 408.9.

Further, from document U.S. Pat. No. 7,666,191 B1 a telemanipulator system is known in which the non-sterile manipulator arms are covered by means of a sterile drape. The coupling unit of the manipulator arm comprises four rotation actuators which are coupled to a first side of a sterile adaptor integrated in the sterile drape. This sterile adapter comprises four integrated rotatably mounted transmitting means which are interconnected between the coupling unit of the manipulator arm and the sterile unit of a surgical instrument.

From document DE 102 42 953 A1, it is known to create a data set of a patient body by means of an imaging method and to represent it in a coordinate system. Further, three reference points which do not lie in one plane are associated with the coordinate system.

When setting up known apparatuses for robot-assisted surgery, the entry points of the surgical instruments are determined for a patient lying on the operating table and, based thereon, the surgical instruments with the instrument tips, which instruments are coupled to the manipulator arms, are oriented with respect to the determined entry points. The orientation of the instruments with respect to a target surgical area is carried out by the user based on his/her wealth of experience. A technical monitoring or a possible control of the orientation of the manipulator arm of the surgical instrument with respect to the target surgical area is not provided in the state of the art.

SUMMARY OF THE INVENTION

It is an aspect of the present invention to specify an apparatus and a method for robot-assisted surgery in which an easy orientation of the surgical instruments including endoscopes with respect to a planned target area is possible.

This aspect is preferably solved by an apparatus and by a method having the features of the independent claims.

An inventive apparatus for robot-assisted surgery has an instrument unit comprising a surgical instrument, the proximal end of which is passable through a body orifice of a patient to a target area defined by the coordinates of a coordinate system of the apparatus.

The apparatus comprises at least one manipulator arm to which the instrument unit is connectable. The apparatus comprises a control unit, which, when the instrument unit is connected to the manipulator arm, determines the distance vector, which is orthogonal to the longitudinal axis of the instrument shaft, between the longitudinal axis and the target area defined by the coordinates, and which generates and preferably outputs a first control information when the amount of the determined distance vector has and/or falls below a first preset value.

By means of such an apparatus for robot-assisted surgery it is achieved that the manipulator arm can easily be positioned such that the instrument unit which is connected to the manipulator arm is in a correct position with respect to a planned entry point in the body of a patient to be operated as well as with respect to a target area defined by coordinates $x_z, y_z, z_z$ in a coordinate system X, Y, Z of the apparatus. The position comprises in particular the location and the orientation of the longitudinal axis of an instrument shaft of a surgical instrument of the instrument unit.

As a result, an easy orientation of the manipulator arm of the apparatus for robot-assisted surgery prior to a surgery on the patient is possible. This makes it possible that the positioning and the orientation of the manipulator arms need not be carried out by a physician but can be carried out by suitable staff. The physician is then only responsible for checking the position of the instrument units. Surgical instruments in the sense of the invention are in particular endoscopes, such as rod endoscopes, or surgical instruments with an end effector.

It is advantageous when the control unit generates and preferably outputs at least a second control information whenever the amount of the determined distance vector has or falls below a second preset value. By means of the second control information thus the correct orientation of the position of the longitudinal axis of the instrument shaft of an instrument unit with respect to the target area can be indicated.

Preferably, the second preset value is zero or a value approximated to the value zero so that the longitudinal axis of the surgical instrument runs through the target area. As a result, a particularly easy positioning of the manipulator arm with respect to its position in space and its orientation with respect to the longitudinal axis of the surgical instrument is possible.

The determined amount of the orthogonal distance vector is preferably the amount of the shortest orthogonal distance vector between the longitudinal axis and the target area.

Further, it is advantageous when the apparatus has an output unit which outputs a first acoustic and/or a first optical signal based on the first control information and/or only outputs a second acoustic or a second optical signal based on the second control information. By means of the optical and/or acoustic signals a user can easily be informed about the correct orientation or the orientation still to be corrected of the instrument unit connected to the manipulator arm so that the correct positioning of the manipulator arm prior to a surgery is assisted in an easy manner.

Further, it is advantageous when the first acoustic signal is a swelling and falling tone or a tone sequence with a first repetition rate and when the second acoustic signal is a continuous tone. The tone sequence preferably comprises several identical tones. The repetition rate can increase with a decrease of the determined amount of the distance vector so that a user is acoustically informed via the repetition rate about an approximation to or a distance from the target area.

The acoustic signal can be output at the control unit or on a control panel.

Alternatively or additionally, the first optical signal can be a blinking light signal with a first blinking rate and the second optical signal can be a continuous light signal. Here, the light of the first light signal and the light of the second light signal can have the same wavelength or the same wavelength spectrum. The blinking signal can in particular be generated by a pulsed ray of light. The continuous light signal can in particular be generated by means of a continuous ray of light. The blinking rate can increase with a decrease in the amount of the distance vector to the target area and decrease with an increase of the amount of the distance vector to the target area. The optical signal can be output at the control unit or on a control panel.

Alternatively or additionally, it is advantageous when, for generating the first optical signal, light with a first wavelength and for generating the second optical signal light with a second wavelength different from the first wavelength is emitted. For generating the optical signals, light with a wavelength in the visible range is used. Preferably, the light of the first wavelength is red light and the light of the second wavelength is green light. In this way, the user obtains an information about the position and orientation of the manipulator arm which can be perceived easily intuitively by means of the light signals. The optical signal can be output at the control unit or on a control panel, in particular on a screen.

Further, it is advantageous when the instrument unit is connectable to the manipulator arm via a sterile lock connected to the coupling unit of the manipulator arm. Via this sterile lock, a sterile separation of the non-sterile coupling unit from the sterile area can be accomplished. When coupling the sterile unit of the instrument unit to the sterile lock, sterile flaps of the sterile lock are preferably opened so that a direct connection between elements of the sterile unit and the coupling unit can be established. Preferably, the sterile unit has sterile flaps which, when connecting the sterile unit to the sterile lock, are opened so that a direct connection between transmitting elements, in particular of mechanical drive elements, between the coupling unit and the sterile unit is possible. After separating the sterile unit from the sterile lock, both the lock flaps and the sterile flaps are again closed, so that both the transmitting elements of the sterile unit and the transmitting elements of the coupling unit are covered in a sterile manner.

A second aspect relates to a method for positioning a manipulator arm in a coordinate system of an apparatus for robot-assisted surgery, in which the coordinates $x_z$, $y_z$, $z_z$ of a target area of a patient are determined. For positioning a manipulator arm of the apparatus for robot-assisted surgery in particular in preparation of a surgery on a patient, an instrument unit is connected to a coupling unit of the manipulator arm. The instrument unit comprises a surgical instrument. The longitudinal axis of the surgical instrument is in particular the longitudinal axis of the instrument shaft of the surgical instrument. When connecting the instrument unit to the manipulator arm, the amount of a distance vector, which is orthogonal to the longitudinal axis, between the longitudinal axis and the target area defined by the coordinates $x_z$, $y_z$, $z_z$ is determined by means of the control unit. A first optical and/or acoustic signal is output, when the determined amount has and/or falls below a first preset value. Thus, it is guaranteed that the longitudinal axis of the surgical instrument runs both through the planned, in particular already marked or existing operative body orifice of the patient and through the target area. As a result, an easy intuitive correct positioning of the manipulator arm in particular in preparation of the apparatus for robot-assisted surgery for a surgery is easily possible. For this, no specifically trained medical staff is required, in particular no physician.

Further, it is advantageous when a second optical and/or acoustic signal is output whenever the determined amount of the distance vector has or falls below a second preset value. Preferably, this second preset value is zero.

The manipulator arm is preferably manually orientated such that the longitudinal axis of the instrument shaft runs through a planned, in particular marked or existing operative body orifice of the patient. For this, the instrument can be oriented such that the instrument tip, in particular an end effector, points at the body orifice or is inserted into a trocar inserted into the body orifice. Further, the manipulator arm is oriented such that the first and/or second optical and/or acoustic signal is output.

It is advantageous when the manipulator arm is oriented in a first step such that the proximal end of the instrument shaft points at a planned or existing operative body orifice of a patient and thus the longitudinal axis of the instrument shaft runs through the planned or existing body orifice. The manipulator arm is then moved in a second step such that the distance, which is determined by the control unit, between the longitudinal axis running through the planned or existing operative body orifice of the patient and the target area defined by the coordinates has or falls below the second preset distance so that the second optical and/or acoustic signal is output. For this, the manipulator arm is moved automatically by the apparatus itself or manually. Likewise, a part of the orientation movement can take place automatically by the apparatus itself and a part of the orientation movement can take place manually by a user.

Alternatively, the manipulator arm can be oriented in a first step such that the amount of the distance vector, which is determined by means of the control unit, between the longitudinal axis and the coordinates $x_z$, $y_z$, $z_z$ of the target area has or falls below the second preset distance. The manipulator arm is then oriented in a second step such that the longitudinal axis runs through the existing or planned, in particular marked operative body orifice of the patient and the longitudinal axis remains oriented to the target area. Here, the manipulator arm can be moved automatically by the apparatus itself and/or manually by a user in the first and/or second step.

By the illustrated solutions of the invention, it is possible to achieve an optimum pre-positioning of the instrument unit by a manual and/or automatic pre-positioning of the manipulator arms of the apparatus for robot-assisted surgery.

The manipulator arm can have a telescopic arrangement for moving the coupling unit in the direction of the telescopic axis of the telescopic arrangement. The telescopic axis runs parallel to the longitudinal axis of the instrument shaft so that the instrument shaft moves along its extended longitudinal axis during extension and retraction of the telescopic arrangement.

By the indicated solutions the user recognizes whether the positioning (instrument tip points at the desired point of entry into the site) and the orientation of the longitudinal axis of the instrument shaft (corresponding color of the optical signal, for example green and/or corresponding tone of the acoustic signal) have been set simultaneously successfully. In this position, a trocar inserted into the site can be connected in a best possible manner to a coupling interface of the manipulator arm optionally provided for this. In any case, in this position the manipulator arm is in a best possible initial position for a planned surgery.

Preferably, the relevant areas of the anatomy of the patient, in particular the target area, are defined by the coordinates $x'_z$, $y'_z$, $z'_z$ in a patient coordinate system $X'$, $Y'$, $Z'$. The coordinate origin of the patient coordinate system $X'$, $Y'$, $Z'$ can, for example, be defined in the crossing point of the median planes with the dorsally lying frontal plane as well as a transverse plane. The coordinates of the patient coordinate system are in a fixed known relation to a coordinate system $X$, $Y$, $Z$ of the apparatus for robot-assisted surgery so that the coordinates $x$, $y$, $z$ of elements of the apparatus can easily be converted into coordinates $x'$, $y'$, $z'$ of the patient coordinate system $X'$, $Y'$, $Z'$, and coordinates $x'$, $y'$, $z'$ of the patient coordinate system $X'$, $Y'$, $Z'$, such as the coordinates $x'_z$, $y'_z$, $z'_z$ of the target area, can easily be converted into coordinates $x_z$, $y_z$, $z_z$ of the coordinate system $X$, $Y$, $Z$ of the apparatus.

For example, the coordinates $x'_z$, $y'_z$, $z'_z$ of a target area in the patient coordinate system $X'$, $Y'$, $Z'$ can be determined in that a manual measuring of the patient, for example by means of a measuring tape, is carried out. Here, a centimeter-precise determination of the coordinates $x_z$, $y_z$, $z_z$ of the target area in the coordinates of the patient coordinate system $X'$, $Y'$, $Z'$ and their transformation into coordinates $x_z$, $y_z$, $z_z$ of the coordinate system $X$, $Y$, $Z$ of the apparatus provides a multiple sufficient accuracy to be able to position and to orient the surgical instrument sufficiently well. Alternatively, the measuring of the target area can also take place directly in coordinates $x_z$, $y_z$, $z_z$ of the coordinate system of the apparatus.

In addition, modern imaging methods, such as the computed tomography or the magnetic resonance tomography, provide data which make a more precise determination of the coordinates in the patient coordinate system $X'$, $Y'$, $Z'$ and, based thereon, in the coordinate system of the apparatus possible.

The shaft of the instrument unit preferably has a length which, in the extended state of the telescopic arrangement of the manipulator arm, is just so long that the proximal end of the instrument shaft is inserted by approximately 1 cm to 5 cm into a trocar inserted into the site. In this state, also a trocar holder optionally present on the manipulator arm can be connected to the trocar. In the retracted state of the telescopic arrangement, the proximal end of the instrument shaft has been moved through the target area. Given such an orientation of the manipulator arm the trocar holder is so to speak automatically correctly positioned for a connection to the trocar when the proximal end of the instrument shaft is inserted into the trocar.

In combination with pre-operatively determined data of the target area, in particular by means of a computed tomography or a magnetic resonance tomography, the position of the extension of the longitudinal axis of the instrument shaft with respect to the target area can be illustrated during a set-up and docking operation by means of the instrument unit according to the afore-described approach on an additional monitor mounted in the field of view of the user. For this, preferably a plane, which is orthogonal to the longitudinal axis of the instrument shaft, through the CT and/or MRT data set of the patient is illustrated. The plane through the CT and/or MRT data set runs through the target surgical area. Thus, the user is given a further decision tool, in addition to the acoustic and optical information about the distance between the longitudinal axis of the surgical instrument and the target area, in order to be able to set up the manipulator arms of the apparatus for robot-assisted surgery for the planned surgery in a best possible manner. The apparatus for robot-assisted surgery preferably has several, in particular four or five manipulator arms, of which preferably one is connected to an endoscope and the further manipulator arms are connected to instrument units with surgical instruments with end effectors for carrying out the surgery. In particular, the manipulator arms provided for the instrument units with these surgical instruments with end effectors are preferably successively positioned and oriented by means of the inventive approach in order to subsequently perform the manipulations required for the surgery. The coordinates of the target area can preferably indicate a spatial area so that the target area relevant for setting up the manipulator arms has a spatial dimension, or can be defined by a point. Likewise, for each surgical instrument a separate target area can be provided, wherein the target areas may at least partially overlap one another.

The control unit of the apparatus for robot-assisted surgery in particular serves
- for the input and storage of the coordinates of the target area in the patient coordinate system and/or coordinate system of the apparatus,
- for the calculation of the orientation of the instrument to be inserted from the positions of the segments of the manipulator arm,
- for the output of the optical and/or acoustic signal such as by the output of the states: light off, only green light on, only red light on; or by the states: white light on, only green light on, only red light on; and/or by the states, tone off, first tone sequence, second tone sequence.

It is particularly advantageous when a trocar holder provided on the manipulator arm is connected in a first step to a trocar inserted into the body of the patient. In a second step, the instrument unit is connected to the coupling unit of the manipulator arm, wherein the proximal end or the tip of an instrument shaft of a surgical instrument of the instrument unit is inserted into an opening of the trocar. After connecting the instrument unit to the coupling unit, the distance vector, which is orthogonal to the longitudinal axis of the instrument shaft of the surgical instrument, between this longitudinal shaft and the target area defined by the coordinates is determined preferably by means of a control unit, and a first control information is generated when the amount of the determined distance vector has and/or falls below a first preset value. Dependent on the first control information preferably an optical and/or acoustic signal is output by means of an output unit.

In an alternative approach, the instrument unit can be connected to the coupling unit of the manipulator arm in a first step and a trocar holder of the manipulator arm can be connected to a trocar inserted into the body of the patient in a second step, wherein when connecting the trocar holder with the trocar, the tip of the instrument shaft of the surgical instrument of the instrument unit is inserted into the opening of the trocar. Thereafter, in a third step, the distance vector is determined as described before between the longitudinal axis of the instrument shaft and the target area defined by the coordinates and when the amount of the determined distance vector has and/or falls below a first preset value, the first control information is generated.

In all afore-described approaches, the staff in the operating area, in particular the auxiliary staff, is assisted in the optimum orientation of the surgical instrument for the respective surgery, without the instrument being inserted into the patient body already beyond the trocar.

An additional control information can be output when the amount of the determined distance vector is higher than the first preset value. Dependent on this additional control information a corresponding additional or alternative signal can be output so that a user is informed that the longitudinal axis is relatively far from the target area.

The change of the orientation and/or position of the instrument unit connected to the coupling unit can take place by manual movements of the manipulator arm such that the distance between the instrument axis and the target area is changed. It is particularly advantageous when the frequency of an output acoustic and/or optical signal indicates whether the distance vector becomes larger or smaller. When reaching or falling below a preset second value for the amount of the distance vector, a second optical and/or acoustic signal is output that signals an optimum orientation of the instrument axis to the target area.

The target area is in particular a target surgical area. Alternatively or additionally, the target area can be defined by a target point, such as by the center point of a target surgical area or by a point dependent on the position of another surgical instrument. When the other surgical instrument is an endoscope already inserted at least in part into the body of the patient, such as a rod endoscope, or another imaging system for capturing images of at least a detail of a target surgical area, it is advantageous when the target area is dependent on the position of the endoscope or the other imaging system. For example, the target area can be defined by a point on the optical axis of the optical elements of the endoscope or the optical axis of the optical elements of the other imaging system. The target point is in particular a point in the depth of field, for example the focal point, or a point between the focal point and the proximal end of the endoscope.

The other imaging system can in particular be an optical system based on non-visible light, in particular an X-ray system, a computed tomography system, a magnetic resonance tomography system or another suitable imaging system.

In general, an end of an arbitrary element facing the patient is considered as proximal. In general, an end of an arbitrary element facing away from the patient is considered as distal.

BRIEF DESCRIPTION OF THE DRAWINGS

Further features and advantages result from the following description which explains the invention in more detail on the basis of embodiments in connection with the enclosed Figures.

FIG. 9 shows a detail of a patient body with four marked positions for planned body orifices of the patient, at which one trocar each is inserted.

FIG. 10 shows an arrangement with a portion of an manipulator arm with a coupling unit and the instrument unit connected to the coupling unit with retracted telescopic arrangement of the manipulator arm according to a second embodiment with a trocar holder.

DETAILED DESCRIPTION OF THE PREFERRED EMBODIMENTS

Figure 1:
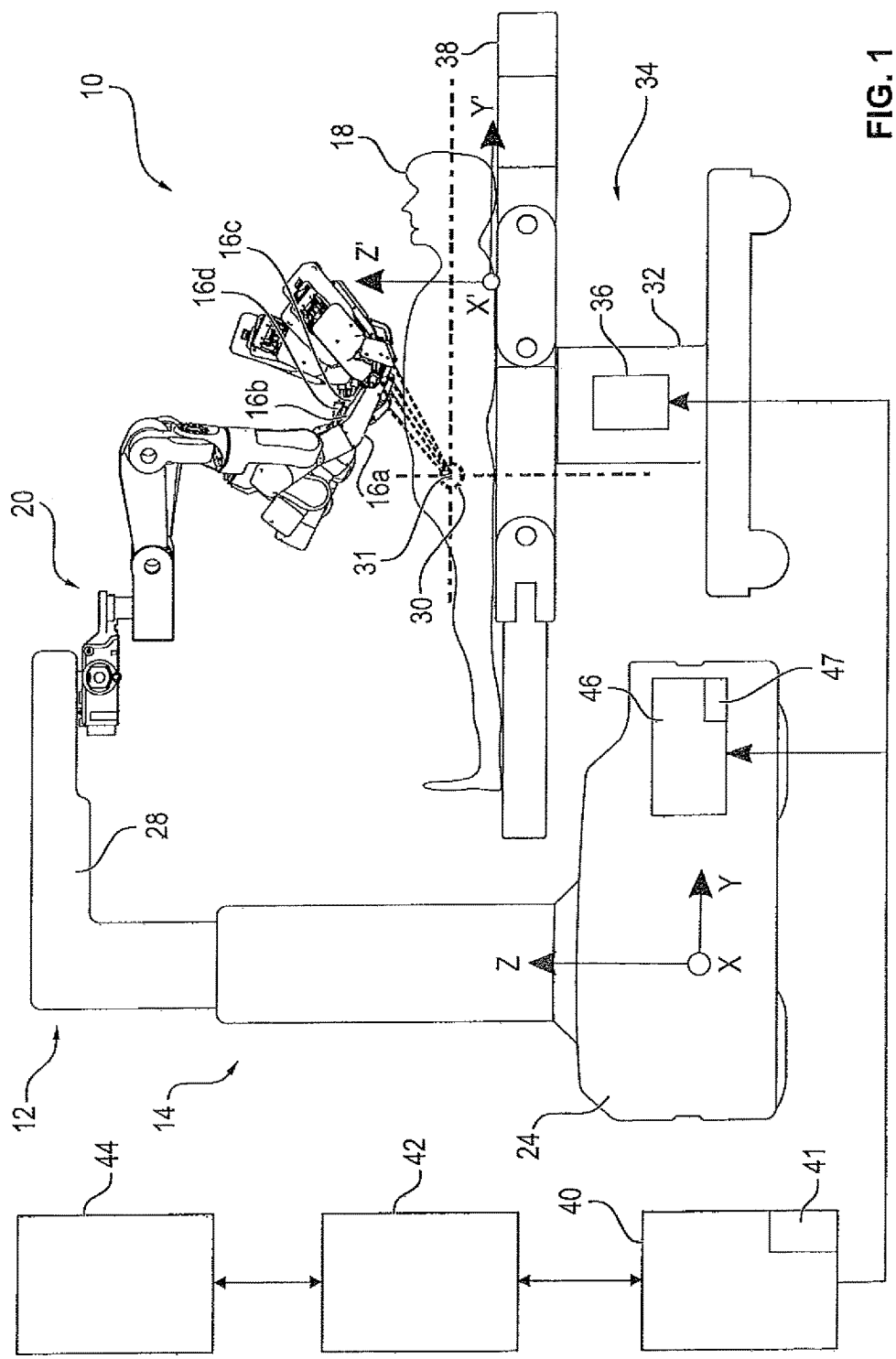
FIG. 1 shows a schematic side view of a system for robot-assisted surgery comprising a manipulator having four manipulator arms, to which one instrument unit each is connectable.

FIG. 1 shows a schematic side view of a system 10 for robot-assisted surgery with a manipulator 12 having a mount 14 and four manipulator arms 16a to 16d. The manipulator 12 is generally also referred to as apparatus for robot-assisted surgery. The system 10 serves to perform a surgery on a patient 18 positioned on an operating table 34. Based on the anatomy of the patient 18 and the operation to be performed, the coordinates $x'_z$, $y'_z$, $z'_z$ of a target surgical area 30 in a patient coordinate system X', Y', Z' have been determined and these coordinates $x'_z$, $y'_z$, $z'_z$ have been stored in a preset manner. The manipulator 12 has a coordinate system X, Y, Z of the apparatus, the coordinate origin of which is arranged in a mount base 24 of a mount 14 of the manipulator 12. The mount 14 has an L-shaped mount arm 28, at the end of which that is remote from the mount base 24 the manipulator arms 16a to 16d are connected via a mount head 20.

The operating table 34 has an operating table column 32 in which a control unit 36 of the operating table 34 is arranged and on which a patient support surface 38 comprising several segments is arranged. The control unit 36 serves to control the movement of elements of the operating table 34, in particular for length adjustment of the operating table column 32 and thus for adjusting the height of the patient support surface 38 and for adjusting individual segments as well as the tilt and the swing of the patient support surface 38. Preferably, however, the adjustment of the segments of the operating table 34 is blocked during a surgery by means of the manipulator 12. The system 10 further comprises a control unit 46 of the manipulator 12 as well as a central control unit 40, the central control unit 40 being connected to the control unit 46 of the manipulator 12, the control unit 36 of the operating table 34 as well as a control panel 42 with a display unit 44 via data lines. The control unit 40 has an output unit 41 and the control unit 46 has an output unit 47, by which optical and/or acoustic signals can be output, respectively.

The surface of the patient support surface 38 forms a frontal plane on which the patient 18 is positioned in a dorsal manner. Further, through the coordinate origin of the patient coordinate system X', Y', Z' a transversal plane in which the coordinate axes X' and Z' lie runs. Further, a median plane in which the coordinate axes Z' and Y' lie runs through the coordinate origin.

The coordinates $x'_z$, $y'_z$, $z'_z$ of the target surgical area 30 in the patient coordinate system X', Y', Z' are known and, due to the known position of the patient coordinate system X', Y', Z' with respect to the coordinate system X, Y, Z of the apparatus 12, they can easily be taken into account in the control of the manipulator arms 16a to 16d as well as the instrument unit connected to the manipulator arms 16a to 16d for performing a surgery by means of the manipulator 12, in particular can be converted into coordinates $x_z$, $y_z$, $z_z$ of the coordinate system X, Y, Z of the apparatus.

The position of the coordinates $y'_z$, $z'_z$ of the center of the target surgical area 30 are indicated in FIG. 1 with respect to the coordinate axes Y' and Z' by means of the broken lines running through the target coordinate area 30.

Figure 2:
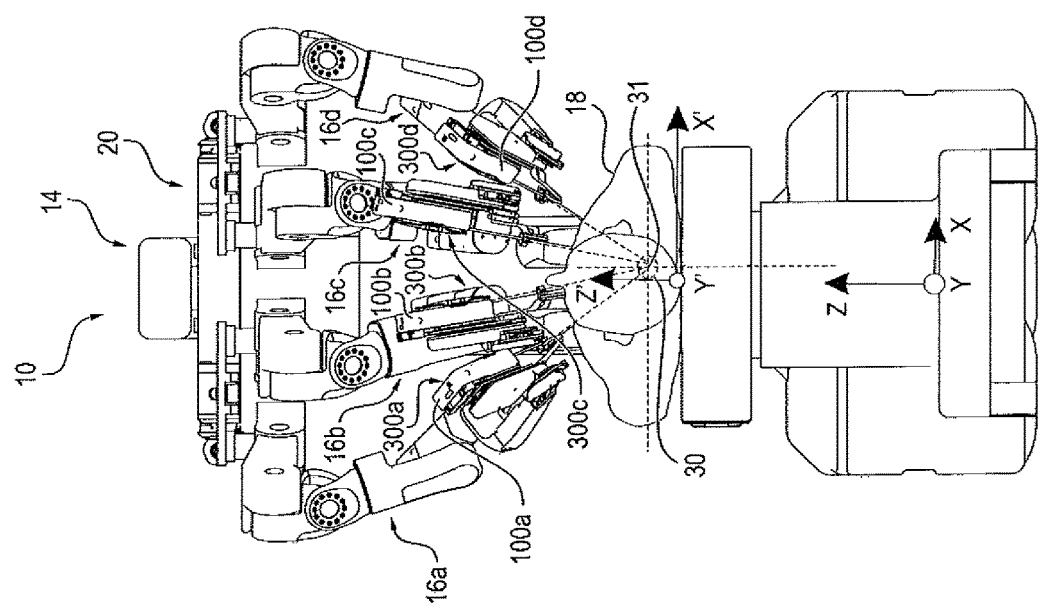
FIG. 2 shows a schematic front view of the system according to FIG. 1.

FIG. 2 shows a schematic front view of the system 10 according to FIG. 1. At the proximal end of the manipulator arms 16a to 16d one coupling unit 100a to 100d is arranged, to each of which one instrument unit 300a to 300d for performing the surgery is connected. The instrument shafts of the respective surgical instrument of the instrument units 300a to 300d are indicated in broken lines, which, in FIG. 2, extend from the coupling units 100a, 100b, 100c, 100d and the sterile units 400a, 400b, 400c, 400d of the instrument units 300a, 300b, 300c, 300d connected to the coupling units 100a, 100b, 100c, 100d and illustrated in FIG. 3 up to the target surgical area 30. The broken lines indicate the longitudinal axes or the extended longitudinal axes of the instrument shafts. By means of the broken lines running through the target surgical area 30 and running parallel to the coordinate axes X' and Z', the coordinates $y'_z$, $z'_z$ of the center 31 of the target surgical area 30 with respect to the coordinate axes X' and Z' are indicated.

In the following, the coupling of the instrument unit 300a to the coupling unit 100a of the manipulator arm 16a via a sterile lock 200a is described with reference to the manipulator arm 16a. The statements apply in the same manner to the further manipulator arms 16b to 16d and to the instrument units 300b to 300d connected to these manipulator arms 16b to 16d via sterile locks 200b to 200d. For simplification, the reference sign digits are used in the following without using the small letters used for distinguishing between the individual manipulator arms.

Figure 3:
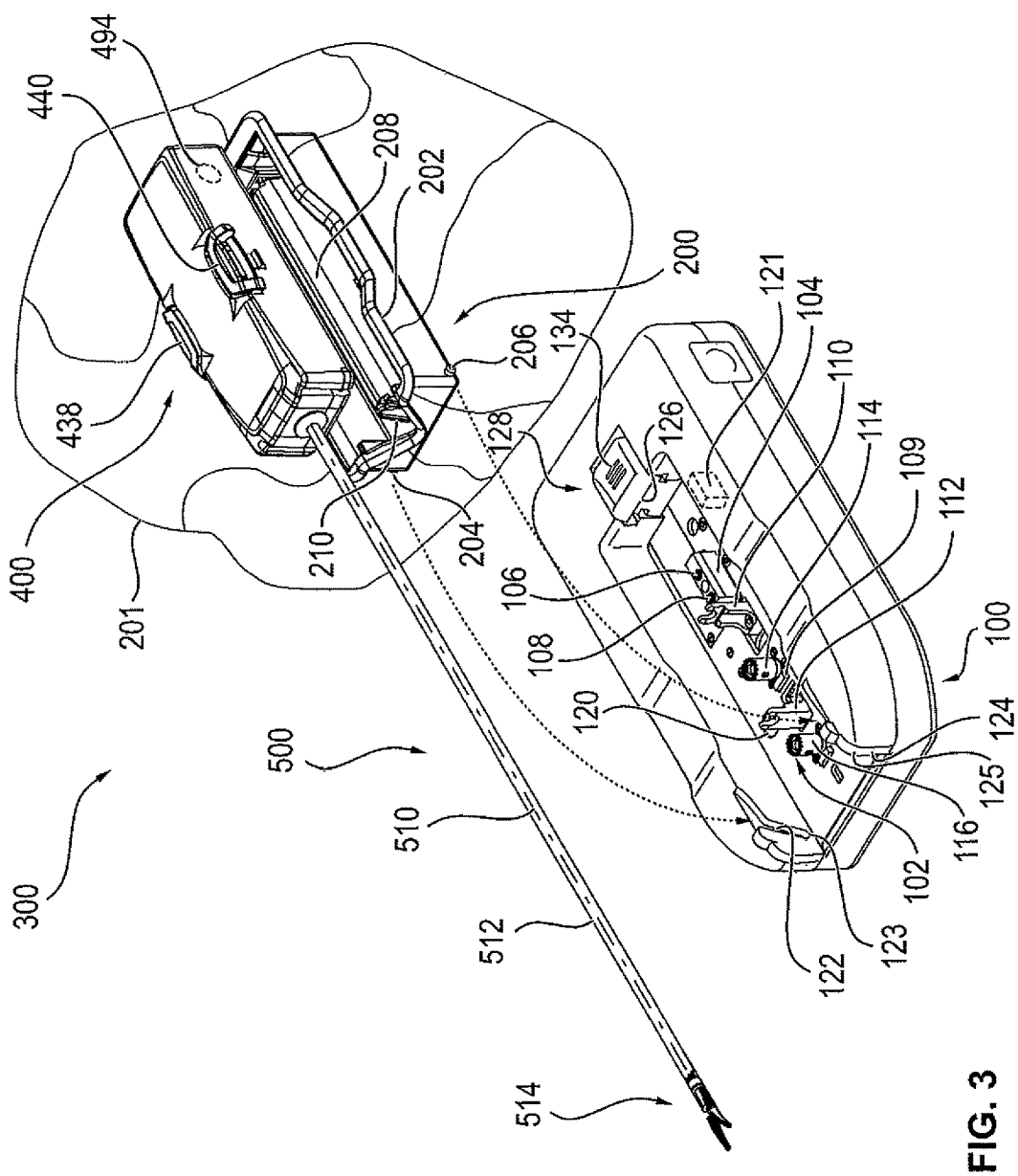
FIG. 3 shows an arrangement for connecting an instrument unit arranged in a sterile area to a non-sterile coupling unit of a manipulator arm.

FIG. 3 shows the coupling unit 100 of the manipulator arm 16, the sterile lock 200 and the instrument unit 300 with the sterile unit 400 and a surgical instrument 500 having an end effector 514. The coupling unit 100, the sterile lock 200 and the instrument unit 300 are shown prior to the connection of the sterile lock 200 to the coupling unit 100 and prior to the subsequent connection of the sterile unit 400 to the sterile lock 200. A flexible sterile sheet designed as a sterile foil 201 is connected to the sterile lock 200 along a circumferential connecting rim 202 of the sterile lock 200 via a suitable connection such as a clamping, adhesive, hook-and-loop, and/or weld connection so that the sterile foil 201 forms together with the sterile lock 200 a closed sterile cover around the areas of the manipulator arm 16 projecting into a sterile operating area.

For a better illustration, only a detail of the sterile foil 201 around the sterile lock 200 is illustrated in FIG. 3. In the following Figures, the sterile foil 201 is partly not illustrated.

For coupling the sterile unit 400 to the coupling unit 100, the sterile lock 200 is arranged between the sterile unit 400 and the coupling unit 100 and enables in the coupled state of the sterile unit 400 to the coupling unit 100 a direct coupling of a first transmitting means 102 of the coupling unit 100 and a second non-illustrated transmitting means of the sterile unit 400.

In the present embodiment, both mechanical energy and electrical energy is transmitted between the coupling unit 100 and the sterile unit 400 by means of the first transmitting means 102. For this, the first transmitting means 102 of the coupling unit 100 has, for example, at least four mechanical drive elements 110 to 116 and the second transmitting means 406 of the sterile unit 400 has four driven elements complementary to the drive elements 110 to 116. Further, the first transmitting means 102 has an electrical transmitting element 104 with two electrical contacts 106, 108 and the second transmitting element has an electrical transmitting element which is complementary to the electrical transmitting element 104 of the first transmitting means 102.

The first transmitting element 102 further comprises an optical transmitting means 109 for transmitting light and/or optical signals. The drive elements of the first transmitting means 102 comprise a first translatory drive element 110 and a second translatory drive element 112, each time for transmitting a translatory movement as well as a first rotatory drive element 114 and a second rotatory drive element 116 for transmitting a rotary motion. The first and the second translatory drive element 110, 112 are each designed as a linear lift fork and the first and the second rotatory drive element 114, 116 are designed as drive pinions with end-side teeth. Further, the coupling unit 100 has a coupling sensor arranged in a recess and detecting a first detection element formed by a first detection pin projecting from the sterile unit 400 when the sterile lock 200 is correctly coupled to the coupling unit 100 and the sterile unit 400 is correctly coupled to the sterile lock 200.

In other embodiments, the first and second transmitting means can also have more or less drive elements, driven elements and electrical transmitting elements which transmit mechanical and/or electrical energy by a direct coupling. Here, as a direct coupling a coupling of the transmitting means is considered, in which no further transmitting elements are provided between the first transmitting means and the second transmitting means for a transmission of mechanical and/or electrical energy and/or optical rays, wherein in particular no electrical, mechanical or optical transmitting elements are provided in a sterile barrier, such as the sterile lock 200, arranged between the coupling unit 100 and the sterile unit 400. The coupling unit 100 further has an RFID read and write unit 121, by means of which an RFID transponder 494 of the sterile unit 400 is readable and/or writable.

For connecting the coupling unit 100 to the sterile lock 200, the coupling unit 100 has opposite guiding grooves 122, 124, into which the guiding pins 204, 206 of the sterile lock 200 are inserted until they have reached the front end 123, 125 of the respective guiding groove 122, 124. At a first end of the sterile lock 200, the guiding pins 204, 206 project outward on opposite sides. Thereafter, the opposite second end of the sterile lock 200 is pushed downward so that the sterile lock 200 is rotated about an axis of rotation running through the guiding pins 204, 206 until a snap-in nose 126 of a snap-in element 128 engages with a complementary snap-in area of the sterile lock 200.

The unlocking button 134 is swivel-mounted about an axis of rotation and is held in its snap-in position shown in FIG. 3 by a spring. For disconnecting the snap-in connection, an unlocking button 134 of the snap-in element 128 is pressed by a finger so that a spring is tensioned and the snap-in element 128 together with the snap-in nose 126 is rotated so that the snap-in nose 126 is disengaged from the complementary snap-in element of the sterile lock 200. As a result, the second end of the sterile lock 200 previously engaged with the snap-in nose 126 can again be pivoted out of the coupling unit 100. After this second end of the sterile lock 200 has been pivoted out of the coupling unit 100, the sterile lock 200 can again be completely separated from the coupling unit 100 in that the sterile lock 200 is pulled out of the guiding grooves 122, 124 along the latter together with the guiding pins 204, 206 engaged with the guiding grooves 122, 124 until the guiding elements 204, 206 are no longer engaged with the guiding grooves 122, 124. Between the guiding grooves 122, 124 and the snap-in element 128, a receiving area formed by a corresponding recess in the housing of the coupling unit 100 is provided, which in the present embodiment surrounds the sterile lock 200 on three sides and at least in part on the bottom side.

The sterile lock 200 has lock flaps 208, 210 which are swivel-mounted via hinges. By means of these hinges the lock flaps 208, 210 can be swiveled from the closed state shown in FIG. 3 into an open state. In the open state of the lock flaps 208, 210 a direct coupling of the first transmitting means 102 of the coupling unit 100 to the second transmitting means of the sterile unit 400 can be accomplished.

On the outsides of the side walls and the end walls of the sterile lock 200 a circumferential edge 202 is formed, with which the sterile foil 201 of the sterile cover is connected in a suitable manner.

The sterile unit 400 further has oppositely arranged snap-in and actuating elements 438, 440, by which an again releasable snap-in connection is established when connecting the sterile unit 400 to the sterile lock 200.

Figure 4:
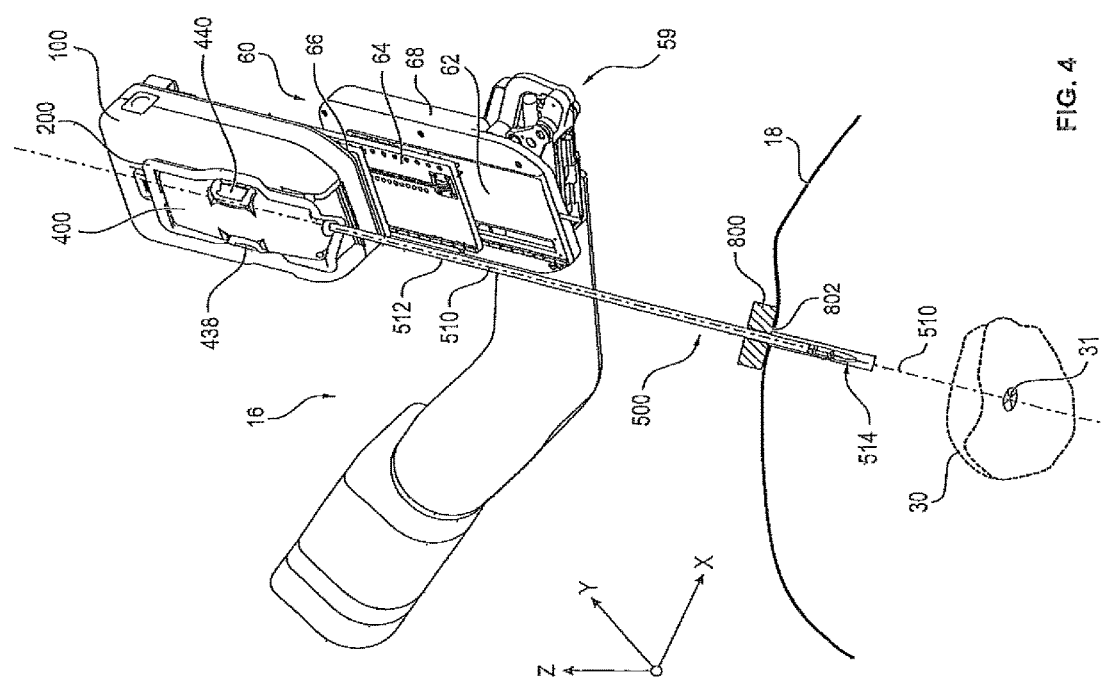
FIG. 4 shows a portion of the manipulator arm with the coupling unit and the instrument unit connected to the coupling unit with an extended telescopic arrangement of the manipulator arm according to a first embodiment.

FIG. 4 shows a portion of the manipulator arm 16, at the proximal end of which the coupling unit 100 is connected via a telescopic arrangement 60. The telescopic arrangement 60 has portions 62, 64, 66 movable with respect to one another and is illustrated in FIG. 4 in an extended state. The portions 62, 64, 66 of the telescopic arrangement 60 can be retracted and extended by means of a drive unit 68 so that the end effector 514 of the surgical instrument 500 can be moved along the longitudinal axis 510 of the instrument shaft 512. The manipulator arm 16 has several segments movable relative to each other, the relative position of which can be changed. The telescopic arrangement 60 is further pivotally coupled via a coupling gear 59 to the further segments of the manipulator arm 16 so that the location and orientation of the longitudinal axis 510 of the instrument shaft 512 of the surgical instrument 500 in its position, i.e. both in its orientation and its location, can be changed by a user input on the control panel 42. For setting up each manipulator arm 16 prior to a surgery, the coupling unit 100 is to be oriented such that the longitudinal axis 510 of the instrument shaft 512 of the surgical instrument 500 connected to the coupling unit 100 runs through a planned or existing body orifice 802 of the patient 18 to be operated and through a defined target surgical area 30. In FIG. 4, a trocar 800 is inserted into the body of the patient 18 at the body entry point 802, through which trocar then the front part of the shaft 512 of the surgical instrument 500 is passed together with the end effector 514 up to the target surgical area 30 for performing the surgery.

Prior to a surgery, the manipulator arm 16 is oriented together with the coupling unit 100 of the manipulator arm 16 automatically or by a user such that the longitudinal axis 510 of the instrument shaft 512 runs through the opening of the trocar 800. Here, the end effector 514 of the surgical instrument 500 can be inserted into the opening of the trocar 800 so that a centered orientation of the longitudinal axis 510 to the desired or existing body entry point 802 takes place. Further, the control unit 46 of the manipulator and/or the central control unit 46 determines the amount of the distance vector between the longitudinal axis 510 of the instrument shaft 514 to the target surgical area 30, in particular the amount of the orthogonal distance vector from the longitudinal axis 510 to the target surgical area 30. Here, it is possible to determine both the amount of the distance vector to the edge of the target surgical area 30 and, alternatively or additionally, the amount of the distance vector to the center 31 of the target surgical area 30.

In the present embodiment, the longitudinal axis 510 runs through the center 31 of the target surgical area 30 so that the amount of the distance vector in the present embodiment between the longitudinal axis 510 and the target surgical area 30 is zero, since the longitudinal axis 510 runs through the target surgical area 30. The distance to the center 31 of the target surgical area 30 is zero as well since the longitudinal axis 510 runs through the center 31 of the target surgical area 30. When the amount of the orthogonal distance vector falls below a first value, a first optical and/or acoustic signal can be output to a user. As soon as the amount of the distance vector reaches or falls below a second value, a second optical and/or acoustic signal can be output. The second value can in particular be zero so that the second optical and/or acoustic signal is output whenever the longitudinal axis 510 runs through the target surgical area 30 or its center 31. Further, dependent on the determined amount of the distance vector, the output optical and/or acoustic signal may change continuously with the changes of the distance or in several steps so that the user is informed acoustically and/or optically whether the longitudinal axis 510 withdraws from the target surgical area 30 or approaches the same. It has to be taken into account that during the orientation of the manipulator arm 16 or during the set-up operation of the device for robot-assisted surgery only the longitudinal axis 510 of the instrument shaft 512 and not the instrument shaft 512 itself runs through the target surgical area 30 or is guided past the target surgical area 30 at a lateral distance.

Figure 5:
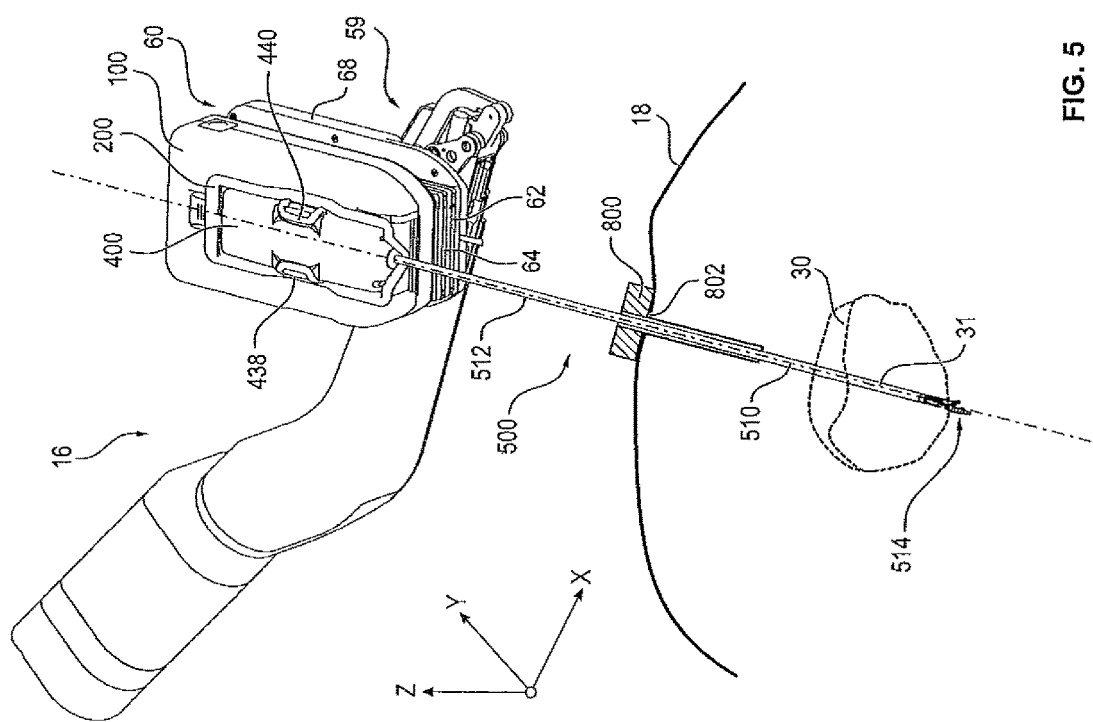
FIG. 5 shows the arrangement according to FIG. 4, wherein the telescopic arrangement is retracted so that the surgical instrument is passed up into the target surgical area or goes beyond it.

FIG. 5 shows the arrangement according to FIG. 4, wherein the portions 62 to 66 of the telescopic arrangement 60 are illustrated in a retracted state, in contrast to FIG. 4. The manipulator arm 16 is preferably positioned such during set-up that the end effector 514 of the instrument shaft 512 of the surgical instrument 500 projects into the trocar 800 inserted into the body of the patient 18 when the telescopic arrangement 60 is retracted. Here, the manipulator arm 16 is positioned such that the end effector 514 projects into the trocar 800 preferably by a length in the range between 1 cm and 5 cm, preferably in a range between 1.5 cm and 3 cm, in particular 2 cm.

From the position shown in FIG. 4, the telescopic arrangement 60 can be retracted so that the end effector 514 of the surgical instrument 500 is passed through the trocar 800 up into the target surgical area 30. As shown in FIG. 5, the end effector 514 can also be moved through the target surgical area 30 in the direction of the longitudinal axis 510 of the instrument shaft 512 and beyond the target surgical area 30.

Figure 6:
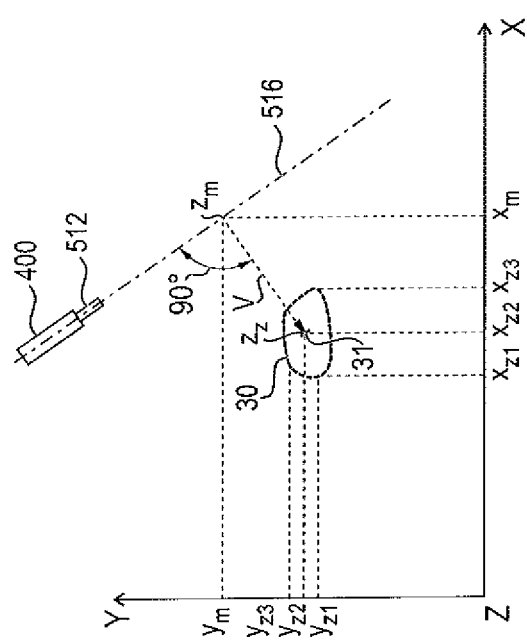
FIG. 6 shows the schematic illustration of the instrument unit and of the target surgical area in a coordinate system of the apparatus.

FIG. 6 shows the schematic illustration of the sterile unit 400 of the instrument unit 300 together with the instrument shaft 512 of the surgical instrument 500 and of the target surgical area 30 in the coordinate system X, Y, Z of the apparatus or the manipulator 12. The spatial extent of the target surgical area 30 has been determined by means of a suitable imaging method for the specific patient 18 and can be defined as a simple geometric body, such as by a sphere, or by the specific spatial extent of a target surgical area 30 determined and/or defined for a specific surgery on the patient 18 by a plurality of coordinates. The target surgical area 30 can be determined for a patient 18 in particular by means of an imaging method or be defined automatically or by a user when evaluating the determined images. As an imaging method, an X-ray method, a computed tomography method, a magnetic resonance method or another suitable method can be used. The external dimensions of the target surgical area 30 are defined in the two-dimensional coordinate system 26 shown in FIG. 11 by the coordinates $x_{Z1}$ and $x_{Z3}$ in X direction as well as by the coordinates $y_{Z1}$ and $y_{Z3}$ on the X axis. The center 31 of the determined target surgical area 30 is defined by the coordinate $x_{Z2}$ on the X axis and $y_{Z2}$ on the Y axis. In the same manner, the spatial extent of the target surgical area 30 on the Z axis running orthogonal to the image plane is known or defined. The coordinates of the point of intersection of the vector V and the longitudinal axis 510 of the instrument shaft 512 are identified in FIG. 6 with $x_m$, $y_m$, $z_m$.

As already explained, the manipulator arm 16 together with the coupling unit 100 is to be positioned prior to a surgery on the patient 18 such that the longitudinal axis 510 of the instrument shaft 512 runs through a desired body orifice 802, and the longitudinal axis 510 runs through the target surgical area 30. In order to in particular assist a user in the correct orientation of the manipulator arm 16 and of the coupling unit 100, the control unit 46 determines the amount of the three-dimensional distance vector V which extends orthogonally to the longitudinal axis 510 along the shortest distance between the longitudinal axis 510 and the center 31 of the target surgical area 30. If the amount of the distance vector V reaches or falls below a first value, a first optical and/or acoustic signal is output, if it reaches or falls below a second value, then a second optical and/or acoustic signal is output so that an optical and/or acoustic information about the correct orientation of the coupling unit 100 is output to the user. As a result, an easy and comfortable possibility has been created to assist a user in the set-up of the manipulator arm 12 and in the positioning of the manipulator arms 16a to 16d prior to the actual surgery.

Figure 7:
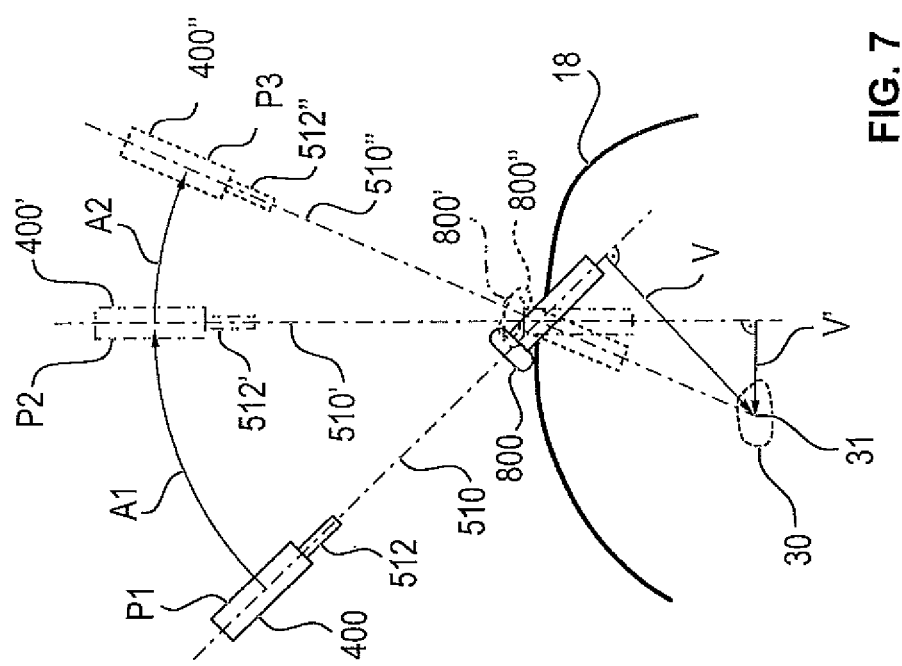
FIG. 7 shows a schematic illustration for the orientation of the instrument unit connected to the manipulator arm with respect to the target surgical area according to a first approach.

FIG. 7 shows a schematic illustration for the orientation of the sterile unit 400 connected to the coupling unit 100 with respect to the target surgical area 30 according to a first approach. In this approach, the manipulator arm 16 together with the coupling unit 100 is oriented in a first step such that the longitudinal axis 510 of the instrument shaft 512 runs through the instrument insertion opening of the trocar 800. With this orientation, the amount of the distance vector V is higher than a preset value so that the control unit 46 generates a control information which indicates that the longitudinal axis 510 does not run through the target surgical area 30. The amount of the distance vector V is, however, so high that it exceeds a first preset value so that neither an optical nor an acoustic signal is output. If the coupling unit 100 is pivoted together with the sterile unit 400 or together with the entire instrument unit 300 from the position P1 in the direction of the arrow A1 to the position P2, the amount of the distance vector V' between the center 31 of the target surgical area 30 and the longitudinal axis 510' of the instrument shaft 512' is lower than a first preset value so that a first acoustic signal is output and/or light of another spectrum and/or a partial spectrum of the light emitted before is emitted so that a user can easily recognize the approximation of the longitudinal axis 510' to the target surgical area 30 on the basis of the change in color. Then, the coupling unit 100 together with the sterile unit 400' is pivoted further from the position P2 in the direction of the arrow A2 until the instrument shaft 512" has reached the position P3 and the amount of the distance vector V' is further reduced until it has in particular reached the value zero so that a second preset value of the amount of the distance vector V' is reached or fallen below. If this is the case, a second optical and/or acoustic signal is output, by which the user is informed about the correct orientation of the longitudinal axis 510" with respect to the target surgical area 30. The second optical signal can have a different wavelength spectrum or a different wavelength with respect to the first optical signal so that the user is informed about the correct orientation of the manipulator arm 16 by the change in color. Alternatively or additionally, the second optical signal can have a different blinking rate with respect to the first optical signal.

When providing two limit values, with which the amount of the distance vector V is compared each time, thus three states are detectable so that a corresponding optical and/or acoustic signal can be output to the user already in the case of an approximation to the target surgical area 30, and a further optical and/or acoustic signal can be output in the case of a correct orientation of the sterile unit 400 with respect to the target surgical area 30. When providing only one limit value, two states can be distinguished, in particular that a distance between the target surgical area 30 and the longitudinal axis 510 exists, i.e. that the longitudinal axis 510 does not run through the target surgical area 30, and the state that the longitudinal axis 510 runs through the target surgical area 30.

Figure 8:
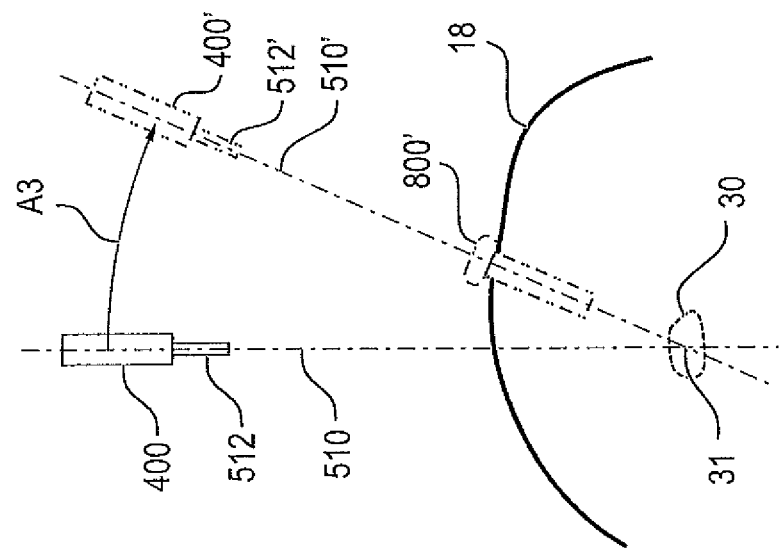
FIG. 8 shows a schematic illustration for the orientation of the instrument unit connected to the manipulator arm with respect to the target surgical area according to a second approach.

FIG. 8 shows a schematic illustration for the orientation of the sterile unit 400 connected to the manipulator arm 16 with respect to the target surgical area 30 according to a second approach, in which, in contrast to the first approach, the longitudinal axis 510 of the instrument shaft 512 is oriented in a first step such that it runs through the target surgical area 30 and a corresponding optical and/or acoustic signal is output to the user. Here, the orientation of the longitudinal axis 510 with respect to the target surgical area 30 can take place such as explained in step 2 of the first approach in connection with FIG. 7. Thus, here too, the user can be informed optically and/or acoustically about the distance and/or the approximation of the longitudinal axis 510 to the target surgical area 30. When the longitudinal axis 510 runs through the target surgical area 30, as shown for the instrument shaft 512 in FIG. 8, the latter is pivoted in the direction of the arrow A3 until the longitudinal axis 510' of the instrument shaft 512' is incident on the instrument opening of the trocar 800.

Unlike as described in connection with FIGS. 7 and 8, the output unit 41, 47 and/or the display unit 44 can also only output an optical and/or acoustic signal or, for example, provide the user with an information via a pulse sequence of the acoustic signal and/or the optical signal, in particular via the pulse width and/or the pulse duration, about how high the amount of the orthogonal distance vector V to the target surgical area 30 and/or to the center 31 of the target surgical area 30 is.

FIG. 9 shows a detail of the body of the patient 18 with four body orifices T1 to T4, into each of which one trocar 800a to 800d is inserted. Through the trocar 800b inserted at the entry point T1, a rod endoscope of the instrument unit 300b connected to the coupling unit 100b of the manipulator arm 16b is inserted into the body of the patient 18. Through the trocar 800a inserted into the body of the patient 18 at the position T2 a surgical instrument 500a of the instrument unit 300a connected to the coupling unit 100a of the manipulator arm 16a is inserted into the body of the patient 18. Through a trocar 800c inserted at the position T3 a surgical instrument 500c of the instrument unit 300c connected to the coupling unit 100c of the manipulator arm 16c is inserted into the body of the patient 18. Through the trocar 800d inserted into the body of the patient 18 at the position T4 a surgical instrument 500d of the instrument unit 300d connected to the coupling unit 100d of the manipulator arm 16d is inserted into the body of the patient 18.

Figure 11:
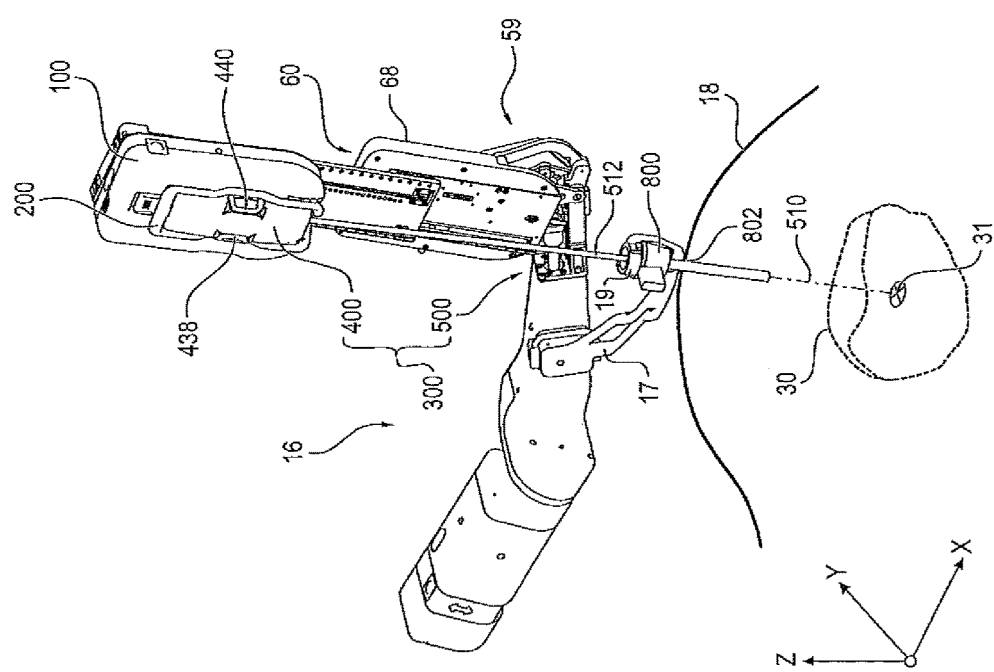
FIG. 11 shows the arrangement according to FIG. 10 with extended telescopic arrangement, wherein the trocar holder of the manipulator arm is connected to a trocar inserted into a patient.

FIG. 10 shows an arrangement with the proximal end of the manipulator arm 16 with the coupling unit 100 and the instrument unit 300 connected to the coupling unit 100 with retracted telescopic arrangement 60 of the manipulator arm 16 according to a second embodiment. The arrangement of the second embodiment according to FIGS. 10 to 12 differs from the first embodiment shown and explained in FIGS. 4 and 5 merely in that a trocar holder 17 is firmly connected to the manipulator arm 16. The trocar holder 17 has a connecting element 19 for connecting the trocar holder 17 to the trocar 800. The positioning and the orientation of the manipulator arm 16 by means of the instrument unit 300 takes place in the same manner as described in connection with the first embodiment. Elements having the same function or the same structure have the same reference signs. In FIG. 11, the arrangement according to FIG. 10 is shown, wherein the trocar holder 17 of the manipulator arm 16 is connected to a trocar 800 inserted into the patient 18 and the telescopic arrangement 60 is in an extended state. The instrument shaft 512 with the end effector 514 is inserted into the instrument opening of the trocar 800 by about 2 cm.

Figure 12:
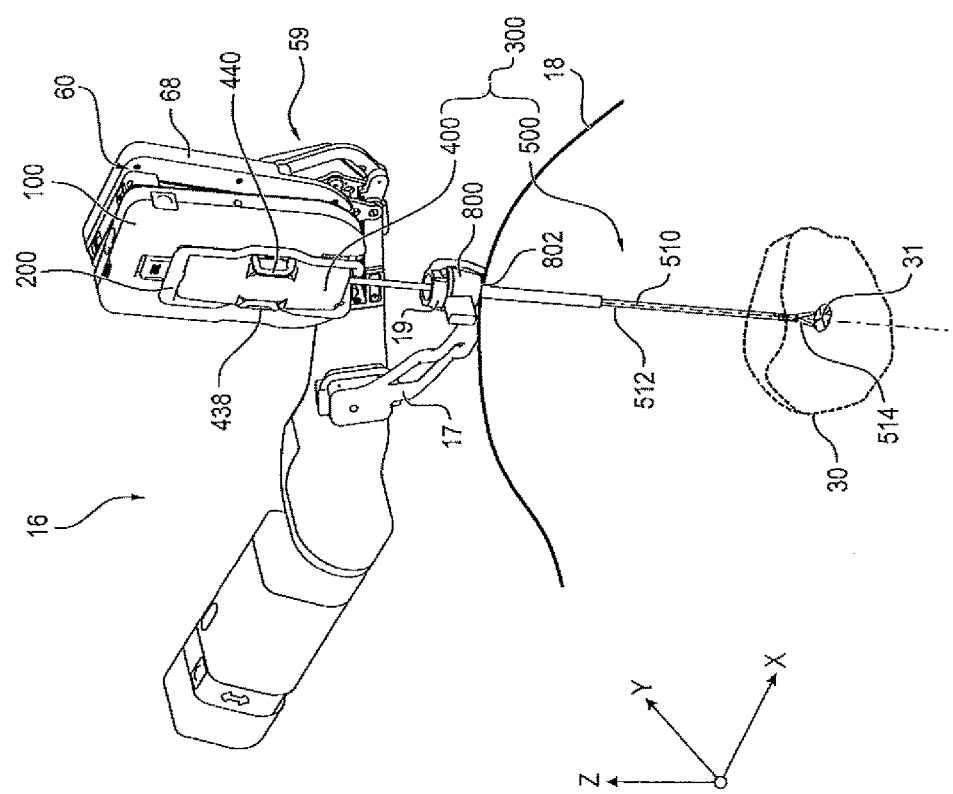
FIG. 12 shows the arrangement according to FIG. 11 with retracted telescopic arrangement.

FIG. 12 shows the arrangement according to FIG. 11, which illustrates the telescopic arrangement 60 in a retraced state. The telescopic arrangement 60 has been moved from the extended position shown in FIG. 11 into its retracted position shown in FIG. 12, without the orientation of the manipulator arm 16 and of the trocar holder 17 having been changed. When retracting and extending the telescopic arrangement 60 a compensation movement by way of a pivoting of the coupling unit 100 with respect to the telescopic arrangement 60 and a pivoting of the telescopic arrangement 60 to the manipulator arm 16 via the coupling gear 59 is implemented so that the surgical instrument 500 can be moved exactly along the longitudinal axis 510 of the instrument shaft 512 when the telescopic arrangement 60 is extended and retracted. The telescopic arrangement 60 can be retracted until the end effector 514 of the surgical instrument 500 has reached the target surgical area 30 or extends beyond the target surgical area 30 in the direction of the longitudinal axis 510 of the surgical instrument 500.

Figure 13:
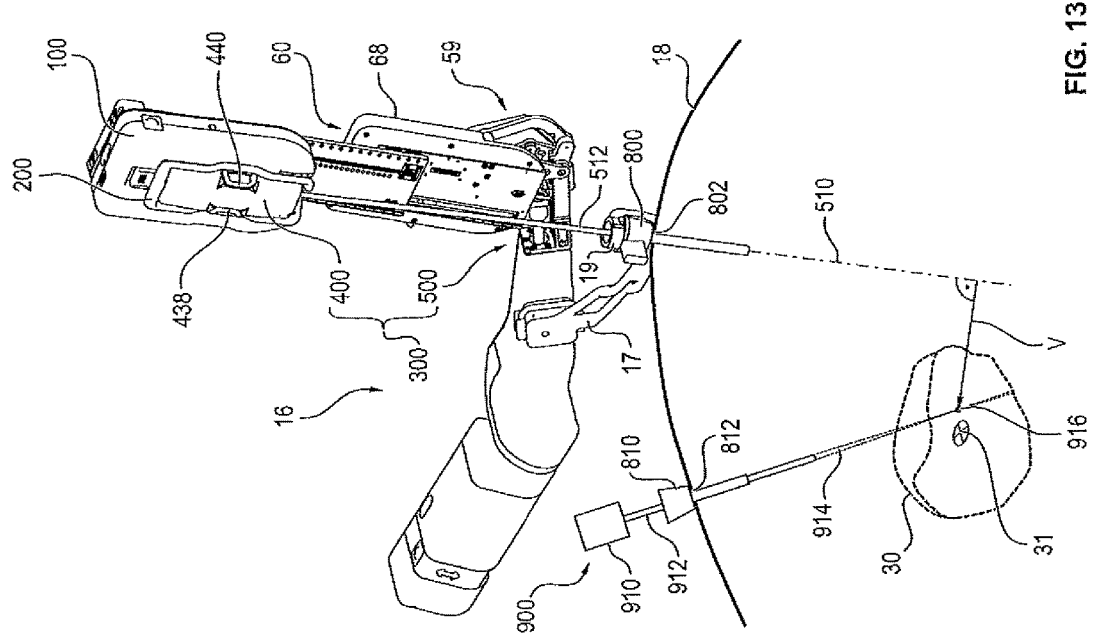
FIG. 13 shows an arrangement with a portion of a manipulator arm with a coupling unit and an instrument unit connected to the coupling unit with extended telescopic arrangement of the manipulator arm according to a third embodiment with a trocar holder for connecting the manipulator arm with a trocar inserted into the body of the patient and with an endoscope at least partly inserted into the body of the patient via a further trocar.

FIG. 13 shows an arrangement with a portion of a manipulator arm 16 with a coupling unit 100 and an endoscope 900 according to a third embodiment. The telescopic arrangement 60 of the manipulator arm 16 is shown in an extended state. An instrument unit 300 with a surgical instrument 500 is coupled to the coupling unit 100. In the third embodiment, too, a trocar holder 17 is provided, which connects a trocar 800 inserted into the body of the patient 18 with the manipulator arm 16. In other embodiments, however, the trocar holder 17 can be dispensed with. The endoscope 900 is a rod endoscope. At least a part of the imaging optics of the rod endoscope 900 is arranged within a rod 912, the proximal end of which is inserted via a trocar 810 via a second body orifice 812 into the body of the patient 18. By means of the rod endoscope 900 images of at least a part of the target surgical area 30 are captured. The rod endoscope 900 has a head portion 910, via which the rod endoscope 900 is connected to the control panel 42 and/or the display unit 44 of the system 10 for robot-assisted surgery. As a result, the image captured by means of the endoscope 900 can be displayed to the user, in particular a surgeon, on the control panel 42 or the display unit 44.

Via the head part 910, the rod endoscope 900 can also be coupled to a further coupling unit 100, in particular a further manipulator arm 16. The ray path 914 of the imaging optics is illustrated by broken lines. The optical axis of the imaging optics of the endoscope 900, i.e. the optical axis of the rod endoscope 900, lies in the center of the ray path 914. The focal point of the imaging optics of the rod endoscope 900 is identified with 916.

In the present embodiment, the orthogonal distance vector V between the longitudinal axis 510 of the instrument shaft 512 of the surgical instrument 500 and the focal point 916 of the imaging optics of the rod endoscope 900 is determined. The focal point 916 thus serves as a target point. The determined orthogonal distance vector V indicates the current distance between the longitudinal axis 510 of the instrument shaft 512 and the focal point 916. The evaluation of the position and the orientation of the manipulator arm 16 with the surgical instrument 500 takes place in the same manner as already explained in connection with the first two embodiments in connection with FIGS. 4 to 12.

Figure 14:
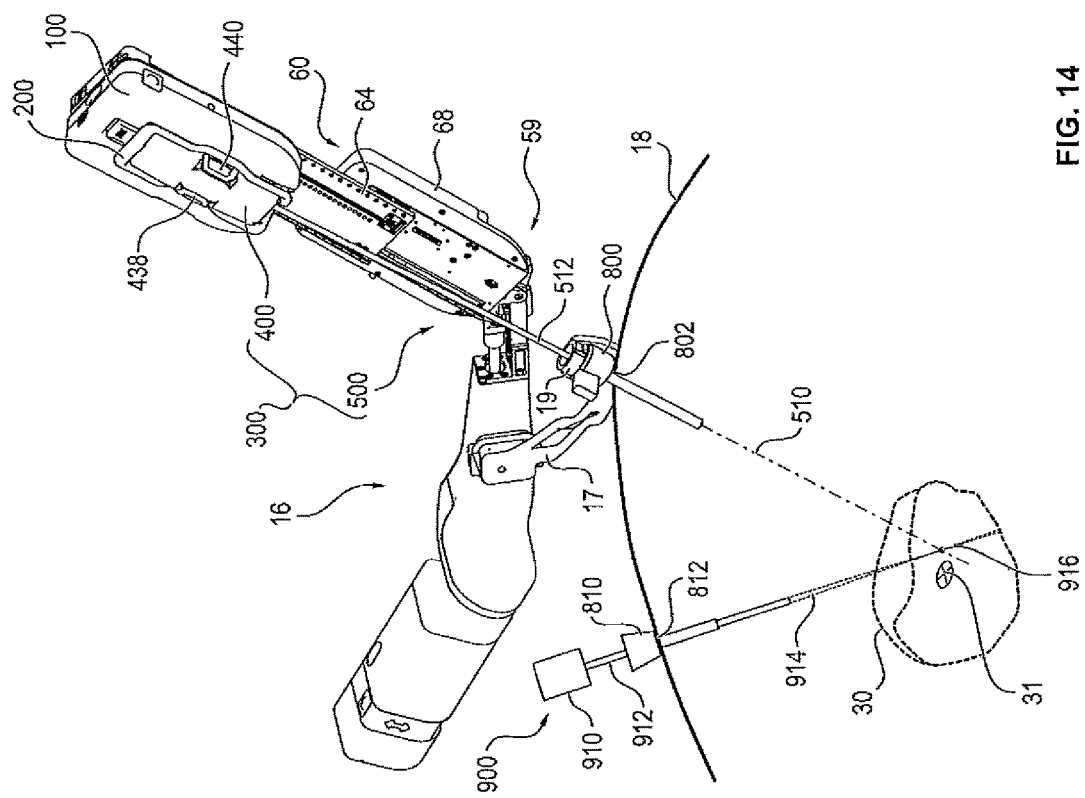
FIG. 14 shows the arrangement according to FIG. 13, wherein the position of the extended telescopic arrangement has been changed by means of a coupling gear so that the longitudinal axis of a surgical instrument of the instrument unit runs to a defined target area in the body of the patient.

In FIG. 13, the proximal end of the instrument shaft 512 with the end effector 514 has been inserted into the instrument opening of the trocar 800. Preferably, the end effector projects by about 2 cm into the instrument opening of the trocar 800. In other embodiments, the tip of the end effector 514 can also be inserted up to the proximal end of the trocar 800 in into its instrument opening or less then 2 cm into the instrument opening of the trocar 800. The telescopic arrangement 60 is in an extended state. Thereafter, the position of the instrument unit 300 coupled to the coupling unit 100 is changed together with at least a part of the segments of the manipulator arm 16 such that the longitudinal axis 510 of the instrument shaft 512 has approached the focal point 916 serving as a target point up to a preset first and/or second distance value, or as shown in FIG. 14, the longitudinal axis 510 of the instrument shaft 512 runs through the focal point 916. For this, in FIG. 14, the telescopic arrangement 60 of the manipulator arm has been pivoted relative to the position shown in FIG. 13 by means of the coupling gear 59.

Figure 15:
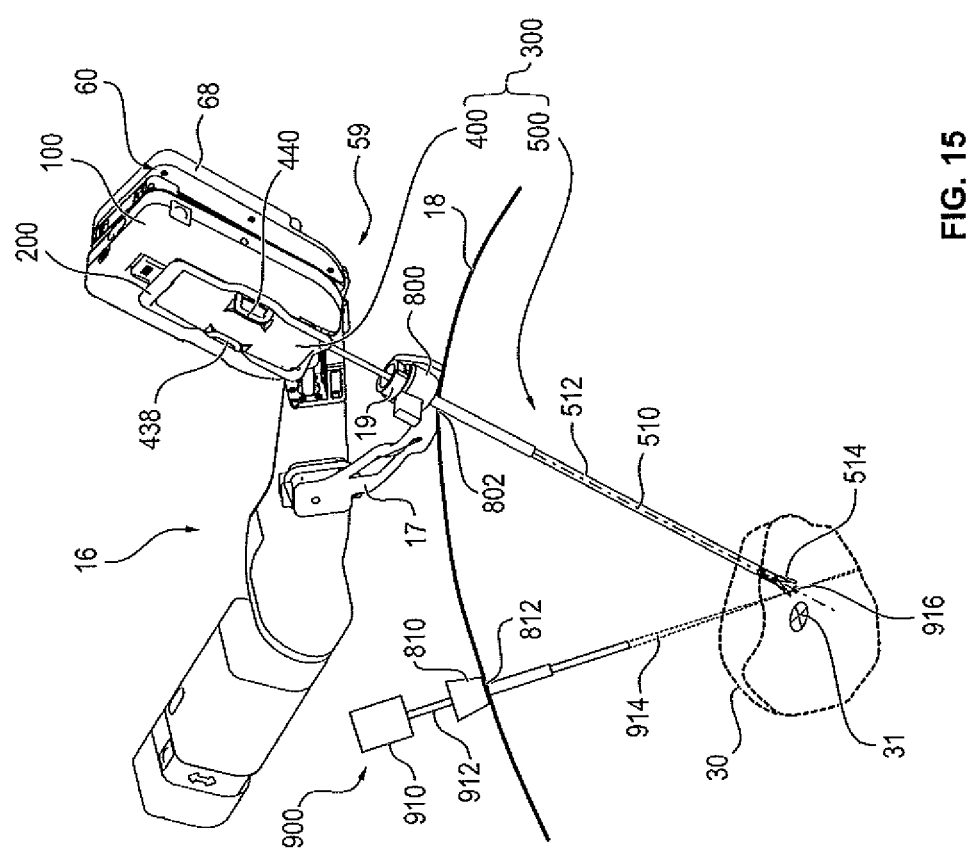
FIG. 15 shows the arrangement according to FIG. 13 with retracted telescopic arrangement.

In FIG. 15, the arrangement according to FIGS. 13 and 14 with retracted telescopic arrangement 60 is shown. By retracting the telescopic arrangement the end effector 514 has been moved up into the field of view of the rod endoscope 900 and into the target surgical area 30, and can be actuated and positioned thereat by visual control. By means of the described approach, it is thus possible to preset the position, i.e. the orientation and the location, of a surgical instrument 500 to be used already such that it is passed to the target surgical area 30 and is reliably brought into the field of view of the rod endoscope 900. The target point or the target area can be defined by coordinates $x_Z$, $y_Z$, $z_Z$ of the coordinate system X, Y, Z of the apparatus or by coordinates $x'_Z$, $y'_Z$, $z'_Z$ of the patient coordinate system X', Y', Z' and, if required, be converted into coordinates of the respective other coordinate system.

Also in the first and the second embodiment according to FIGS. 4 to 12, a target point, such as the center 31 of the defined target surgical area 30 or a target point dependent on the location of the other surgical instrument 900, can be defined instead of the target surgical area 30. Further, instead of the endoscope 900, in the third embodiment another imaging system for capturing images of at least a detail of a target surgical area 30 can be used. The target area is then dependent on the location of the other imaging system. The target point is in particular a point in the depth of field of the imaging optics of the endoscope or the imaging system, such as the focal point of the imaging optics or a point between the focal point and the proximal end of the endoscope 900. The target area can alternatively or additionally be defined by a distance around a point.

LIST OF REFERENCE SIGNS 10 system
12 manipulator
14 mount
16, 16a to 16d manipulator arm
17 trocar holder
18 patient
19 connecting element
20 mount head
24 mount base
28 mount arm
30 target surgical area
31 center of the target surgical area
32 operating table column
34 operating table
36 control unit of the operating table
38 patient support surface
40 central control unit of the apparatus
41 output unit
42 control panel
44 display unit
46 control unit of the manipulator
47 output unit
59 coupling gear
60 telescopic arrangement
62, 64, 66 portions of the telescopic arrangement
68 drive unit
100, 100a to 100d coupling unit
102 first transmitting means
104 electrical transmitting means
106, 108 electrical contact
109 optical transmitting means
110 first translatory drive element
112 second translatory drive element
114 first rotatory drive element
116 second rotatory drive element
120 coupling sensor
121 RFID read and write unit
122, 124 guiding groove
123, 125 front end of the guiding groove
126 snap-in nose
128 snap-in element
134 unlocking button
200 sterile lock
201 sterile foil
202 connecting rim
204, 206 guiding pin
208, 210 lock flap
300, 300a to 300d instrument unit
400, 400a to 400d
400', 400" sterile unit
438, 440 snap-in and actuating element
494 RFID transponder
500, 500a to 500d surgical instrument
510, 510', 510" longitudinal axis
512 instrument shaft
514 end effector
800 trocar
802 body orifice
810 trocar
812 body orifice
900 rod endoscope
910 head part
912 rod
914 ray path
916 focal point
A1 to A3 direction of movement
P1 to P3 position
T1 to T4 planned body orifice
V, V' distance vector $x_Z$, $y_Z$, $z_Z$ coordinates of the target area in the coordinate system of the apparatus X, Y, Z coordinate system of the apparatus X', Y', Z' patient coordinate system $x'_Z$, $y'_Z$, $z'_Z$ coordinates of the target area in the patient coordinate system

What is claimed is:

1. An apparatus for robot-assisted surgery, comprising
an instrument unit having a surgical instrument with an instrument shaft, the proximal end of which is passable through a body orifice of a patient to a target area defined by coordinates ($x_z$, $y_z$, $z_z$) of a coordinate system (X, Y, Z) of the apparatus,
at least one coupling unit of a manipulator arm, to which optionally the instrument unit is connectable,
a control unit,
which, when the instrument unit is connected to the coupling unit, determines the distance vector (V), which is orthogonal to the longitudinal axis of the instrument shaft of the surgical instrument, between the longitudinal axis and the target area defined by the coordinates ($x_z$, $y_z$, $z_z$),
which generates a first control information when the amount of the determined distance vector (V) has and/or falls below a first preset value, and
comprising an output unit which outputs a signal dependent on the first control information.

2. The apparatus according to claim 1, wherein the control unit generates at least a second control information, when the amount of the determined distance vector (V) has and/or falls below a second preset value, and that the output unit outputs a signal.

3. The apparatus according to claim 1, wherein the output unit of the apparatus outputs a first acoustic and/or a first optical signal on the basis of the first control information, and/or that the output unit outputs only a second acoustic and/or only a second optical signal on the basis of the second control information.

4. The apparatus according to claim 3, wherein the first acoustic signal is a swelling and falling tone or a tone sequence with a first repetition rate and that the second acoustic signal is a continuous tone.

5. The apparatus according to claim 3, wherein the first optical signal is a blinking light signal with a first blinking rate and that the second optical signal is a light signal with a second blinking rate, which may also be zero.

6. A method for positioning a manipulator arm in a coordinate system (X, Y, Z) of an apparatus for robot-assisted surgery, comprising:
in which the coordinates ($x_z$, $y_z$, $z_z$) of a target area in a patient are determined,
in which for positioning a manipulator arm an instrument unit is connected to a coupling unit of the manipulator arm,
wherein the instrument unit comprises a surgical instrument having an instrument shaft with a longitudinal axis,
in which, when the instrument unit is connected to the coupling unit, the distance vector (V), which is orthogonal to the longitudinal axis, between the longitudinal axis and the target area defined by the coordinates ($x_z$, $y_z$, $z_z$) is determined by means of a control unit, and
in which a first optical and/or acoustic signal is output by means of an output unit when the amount of the determined distance vector (V) has and/or falls below a first preset value.

7. The method according to claim 6, wherein a second optical and/or acoustic signal is output when the amount of the determined distance vector (V) has reached and/or falls below a second preset value.

8. The method according to claim 6, wherein the manipulator arm is oriented such that the longitudinal axis of the instrument shaft runs through a planned or actual operative body orifice of a patient and the first and/or second optical and/or acoustic signal is output.

9. The method according to claim 6, wherein the manipulator arm is oriented in a first step such that the longitudinal axis of the instrument shaft runs through a planned or existing operative body orifice of the patient, and that the manipulator arm is moved in a second step until the amount of the distance vector (V), determined by means of the control unit, between the longitudinal axis running through the planned or existing operative body orifice of the patient and the target area defined by the coordinates ($x_z$, $y_z$, $z_z$) reaches or falls below the first and/or second value,
wherein the manipulator arm is moved automatically by the apparatus itself and/or manually.

10. The method according to claim 6, wherein the manipulator arm is oriented in a first step such that the amount of the distance vector (V), which is determined by means of the control unit, between the longitudinal axis and the target area defined by the coordinates ($x_z$, $y_z$, $z_z$) reaches and/or falls below the first and/or second value,
and that the manipulator arm is oriented in a second step such that the longitudinal axis of the instrument shaft runs through the existing or planned operative body orifice of the patient,
wherein the manipulator arm is moved automatically by the apparatus itself and/or manually.

11. The method according to claim 6, wherein the proximal end of the instrument shaft is inserted into the body orifice of the patient or into a trocar inserted into the patient.

12. The method according to claim 11, wherein the proximal end of the instrument shaft (512) is inserted into the body orifice or the trocar after the manipulator arm has been oriented according to claim 9 or claim 10.

13. The apparatus according to claim 1 wherein the target area is defined by a target surgical area, by a center of a target surgical area or by the position of another surgical instrument.

14. The apparatus according to claim 1, wherein the target area is defined by the position of an endoscope at least partly inserted into the body of the patient or another imaging system for capturing images of at least a detail of a target surgical area, preferably by the optical axis and/or the focal point of the imaging optics of the endoscope or the imaging system.

15. The method according to claim 6 wherein the target area is defined by a target surgical area, by a center of a target surgical area or by the position of another surgical instrument.

16. The method according to claim 6, wherein the target area is defined by the position of an endoscope least partly inserted into the body of the patient or another imaging system for capturing images of at least a detail of a target surgical area, preferably by the optical axis and/or the focal point of the imaging optics of the endoscope or the imaging system.

* * * * *